(12) United States Patent
Klawunder

(10) Patent No.: US 8,164,625 B2
(45) Date of Patent: Apr. 24, 2012

(54) DEVICE AND METHOD FOR VISUALLY RECORDING TWO-DIMENSIONAL OR THREE-DIMENSIONAL OBJECTS

(75) Inventor: Dieter Klawunder, Reichshof (DE)

(73) Assignee: Modi Modular Digits GmbH, Reichshof (DE)

( * ) Notice: Subject to any disclaimer, the term of this patent is extended or adjusted under 35 U.S.C. 154(b) by 1126 days.

(21) Appl. No.: 11/922,752

(22) PCT Filed: Jun. 26, 2006

(86) PCT No.: PCT/EP2006/006125
§ 371 (c)(1),
(2), (4) Date: Dec. 21, 2007

(87) PCT Pub. No.: WO2007/000293
PCT Pub. Date: Jan. 4, 2007

(65) Prior Publication Data
US 2010/0118121 A1 May 13, 2010

(30) Foreign Application Priority Data
Jun. 25, 2005 (DE) .......................... 10 2005 029 901

(51) Int. Cl.
*H04N 7/18* (2006.01)
(52) U.S. Cl. ...................... 348/125; 348/142; 356/237.5
(58) Field of Classification Search .................. None
See application file for complete search history.

(56) References Cited

U.S. PATENT DOCUMENTS

| | | | |
|---|---|---|---|
| 3,891,795 A | 6/1975 | Johnson et al. | |
| 4,337,482 A | 6/1982 | Coutta | |
| 4,963,962 A | 10/1990 | Kruegle et al. | |
| 5,173,796 A | 12/1992 | Palm et al. | |
| 5,276,546 A | 1/1994 | Beaty et al. | |
| 6,061,086 A | 5/2000 | Reimer et al. | |
| 6,144,452 A | 11/2000 | Hachiya | |
| 6,166,393 A | 12/2000 | Paul et al. | |
| 6,370,329 B1 | 4/2002 | Teuchert | |
| 6,448,549 B1 | 9/2002 | Safaee-Rad | |
| 6,633,376 B1 | 10/2003 | Nishida et al. | |
| 7,365,837 B2* | 4/2008 | Jeong ......................... | 356/237.5 |

(Continued)

FOREIGN PATENT DOCUMENTS

DE 696 10 925 6/2001

(Continued)

*Primary Examiner* — Patrice Winder
(74) *Attorney, Agent, or Firm* — Hudak, Shunk & Farine Co. LPA

(57) ABSTRACT

A device for visually recording two-dimensional or three-dimensional objects, which comprises a camera for recording images of the two-dimensional or three-dimensional object and which is provided with, can be connected to or is connected to at least one evaluation unit for evaluating the recorded images. A single camera and at least one adjustable or pivotal mirror element are provided. According to the method for visually recording two-dimensional or three-dimensional objects while using a device of the aforementioned type, a camera and at least one adjustable mirror element are arranged relative to one another so that the objects to be recorded are situated in the coverage area of the at least one mirror element. The adjustable mirror element for recording the objects to be recorded is displaced or pivoted about one or two axes with an adjustable velocity. The camera records the objects projected in the at least one mirror element, and the recorded objects are routed from the camera to an evaluation unit for evaluation and are processed.

22 Claims, 2 Drawing Sheets

U.S. PATENT DOCUMENTS

| | | | |
|---|---|---|---|
| 7,446,864 B2 * | 11/2008 | Okabe et al. | 356/237.1 |
| 7,646,477 B2 * | 1/2010 | Yoshida et al. | 356/237.5 |
| 7,969,565 B2 * | 6/2011 | Stober | 356/237.2 |
| 2004/0085443 A1 * | 5/2004 | Kallioniemi et al. | 348/135 |
| 2004/0197019 A1 | 10/2004 | Van Den Broek et al. | |
| 2005/0025353 A1 * | 2/2005 | Kaneko et al. | 382/152 |
| 2006/0072105 A1 | 4/2006 | Wagner | |

FOREIGN PATENT DOCUMENTS

| | | |
|---|---|---|
| DE | 697 03 487 | 6/2001 |
| DE | 69610925 T2 | 6/2001 |
| DE | 69703487 T2 | 6/2001 |
| DE | 198 83 004 | 7/2001 |
| DE | 19883004 T1 | 7/2001 |
| DE | 101 04 355 | 9/2001 |
| DE | 10104355 A1 | 9/2001 |
| DE | 697 10 714 | 10/2002 |
| DE | 69710714 T2 | 10/2002 |
| DE | 101 46 158 | 4/2003 |
| DE | 10146158 A1 | 4/2003 |
| DE | 203 17 095 | 4/2004 |
| DE | 20317095 U1 | 4/2004 |
| DE | 10 2004 004 278 | 8/2004 |
| DE | 102004004278 A1 | 8/2004 |
| DE | 103 52 936 | 12/2004 |
| DE | 10352936 A1 | 12/2004 |
| JP | 52-67511 | 4/1977 |
| JP | 52-067511 A | 6/1977 |
| JP | 63-129473 | 1/1988 |
| JP | 63-129473 A | 6/1988 |
| JP | 63-167981 A | 7/1988 |
| JP | 63-167981 | 12/1988 |
| JP | 11-037723 A | 2/1999 |
| JP | 11-37723 | 12/1999 |
| WO | WO 2004/032592 * | 4/2004 |

* cited by examiner

DEVICE AND METHOD FOR VISUALLY RECORDING TWO-DIMENSIONAL OR THREE-DIMENSIONAL OBJECTS

FIELD OF INVENTION

The present invention relates to a device and a method for visually recording two-dimensional or three-dimensional objects, the device comprising a camera for recording images of the two-dimensional or three-dimensional object and being provided with or connectable or connected to at least one analysis unit for analyzing the recorded images.

BACKGROUND OF THE INVENTION

In many cases, products are subjected to a quality control after their production to be able to detect possible flaws. Various methods and devices are known here in the prior art precisely for checking surfaces and connections between components, which usually use multiple cameras for the examination. For example, soldered joints are checked in that a camera records a soldered object and makes a decision in regard to the quality of the soldered joint via a corresponding analysis program on a computer. A corresponding method and a device are described in DE 10 2004 004 278 A1. In addition to the camera, a handling device is provided therein to move the soldered object in relation to the stationary camera. The handling device grips the circuit board to be evaluated and rotates it appropriately in front of the camera.

The use of a recording unit for three-dimensional images for executing line scanning in an equipping device for electronic components for automatically equipping circuit boards with electronic components is known from DE 697 10 714 T2. Displacement of the recording unit in the x and y directions over the circuit board to be equipped is provided for this purpose.

A device and a method for automatically inspecting moving surfaces is known from DE 697 03 487 T2. Three different illumination/observation channels are used for this purpose.

Furthermore, methods and devices for checking bottles having a threaded section are known from DE 696 10 925 T2, for example. In these methods, the bottles move along a high-speed line, video images being recorded of each bottle, the pixels of the particular video image being processed, and the pixels being examined in interesting areas of interest, which were previously selected, to detect thread defects in general over the circumference of the bottle.

DE 203 17 095 U1 discloses a device for recognizing flaws of an object surface in cast parts in particular, a light source for illuminating the object, a light detector for recording a beam reflected from the object surface toward the illumination beam, and an analysis unit for analyzing the image data thus received for error recognition being provided. In the analysis, the number of pixels to be examined and the size of the pixel regions to be considered are to be kept as small as possible. Among all recorded pixels, those whose brightness values deviate from a mean pixel brightness by more than a predefinable tolerance value are ascertained.

The use of a laser beam for scanning a circuit board for its examination is also known, e.g., from DE 198 83 004 T1, in which the scanning device comprises two galvanic mirrors having rotating shafts orthogonal to one another and a scanning lens.

The use of six cameras for quality checking in wafers is disclosed in DE 103 52 936 A1, two camera systems being oriented vertically from above on the upper edge zone of the wafer, two camera systems being oriented from below on the lower edge zone, and two camera systems being oriented horizontally on the lateral edge of the wafer. Defects are detected using automatic classification.

DE 101 04 355 A1 discloses a device and a method for image scanning of the surface of an object, for use in a lacquering line for determining contaminants and/or flaws of the surfaces of an object. The device comprises a recording system and a controllable transport medium, the transport medium being able to be moved linearly along a horizontal axis in relation to the recording system and the recording system being able to be moved along a second vertical axis using a travel medium. The recording system comprises a camera and a light.

The devices and methods of the prior art described above each have the disadvantage that the achievable precision of the recorded information is not especially high and the speed of the image recording is also quite low. Critical image recording in particular, as when reading out codes on circuit boards which are positioned at different points, is not possible using these devices of the prior art.

SUMMARY OF THE INVENTION

The present invention is therefore based on the object of refining a device and a method for visually recording two-dimensional or three-dimensional objects in such a way that more rapid and precise recording of objects than in the prior art is possible with low technical outlay during a single recording procedure. The device is also to be equipped suitably precisely for its use for recording codes on circuit boards which are attached to diverse different points on the circuit boards, and/or of soldered points.

The object is achieved by a device for visually recording two-dimensional or three-dimensional objects, which comprises a camera for recording images of the two-dimensional or three-dimensional object and is provided with or connectable or connected to at least one analysis unit for analyzing the recorded images, wherein a single camera and at least one adjustable or pivotable mirror element are provided. For a method for visually recording two-dimensional or three-dimensional objects using a device, the object is achieved in that a camera and at least one adjustable mirror element are situated in relation to one another in such a way that the objects to be recorded are positioned in the recording area of the at least one mirror element, the adjustable mirror element is adjusted or pivoted around one or two axes at an adjustable speed to record the objects to be recorded, the camera records the objects imaged in the at least one mirror element, and the recorded objects are relayed from the camera to an analysis unit for analysis and processed therein. Refinements of the present invention are defined in the dependent claims.

A device for visually recording two-dimensional or three-dimensional objects is thus provided, which does not have a moved camera. A camera is understood in the present case as a device for converting a recorded two-dimensional image into electrical signals. By providing an unmoved camera, the precision of the images may be significantly increased in relation to the prior art, which comprises moved cameras. Upon movement of a camera during a recording or before and/or after, the moved masses must first come to rest before a further recording to avoid corruption of the recording. However, this is usually not the case, because otherwise the recordings would take too long a time. If the precision is to be increased and/or due to the moved mass of the camera, the speed of the recording with a moved camera is much lower than with a fixed camera, because in the latter the camera mass does not have to be accelerated and braked again, which always results in a delay of the following movement. Providing a moved object to be recorded also results in problems in the recording, because distortions may occur as a result of the movement of the object. Furthermore, the construction of such a device is complex, because a handling unit must be provided for moving the object in front of the camera. By the use according to the present invention of a rapidly pivotable mirror element which is lightweight in relation to the camera as the single moved element, the speed of the recording of objects and the precision of the recorded information may be increased very greatly in relation to the prior art by the suitable selection of its mass. Preferably speeds of at least 20 objects per second, especially preferably 50 objects per second, are possible at a precision of $1/100$ mm, in particular even $1/1000$ mm or even better. Recording fewer than 20 objects per second is also possible, as well as an arbitrary number of objects greater than 20 or even greater than 50 per second. This is not possible either with devices of the prior art which use multiple cameras, or with devices of the prior art which use one camera displaceable in the x and y directions.

Fundamentally, one or more than one mirror elements or also a multipart mirror element may be assigned to one camera, if advantages in the recording of the information about the objects to be recorded results due to the multiple parts or the further mirror elements. The recording of the data recorded by the mirror element(s) by the camera is then adapted correspondingly to the number of the mirror elements and their position in space, to be able to receive all information optimally.

It has been proven to be especially advantageous to provide the camera as fixed and to provide an adjustment unit for the mirror element for adjusting or pivoting the mirror element around two axes. In this way, the mirror element may be rotated especially well in one plane around all axes, so that in spite of the good mobility, it also has good stability of its movement. In particular, the distance to the object to be recorded does not change in the z direction, so that a preset or pre-settable focusing in regard to the object is maintained during the recording procedure. With a sufficient distance of the mirror element from the surface of the object, even larger objects, such as circuit boards, etc., may be recorded completely in one recording step or scanning procedure. For example, recording an area of 60×60 cm is possible without problems in one scanning procedure.

To ensure a movement of the mirror element tailored to the object to be recorded, an activation unit is preferably provided for activating the adjustment unit for the mirror element using a predefinable or predefined program. This program may run on a computer assigned to the device or integrated therein and may be tailored to the distance to the object, the desired precision of the recording, and the type of the object and the number of partial areas of the object to be recorded.

The adjustment unit advantageously comprises at least one unit for adjusting the mirror element around the x axis and at least one unit for adjusting the mirror element around the y axis, the units being able to be provided separately from one another or in combination with one another. In particular, it has proven to be advantageous to design the x axis adjustment unit for adjusting the mirror element around the x axis and/or the y axis adjustment unit for adjusting the mirror element around the y axis as drivable or driven by motor, hydraulically, pneumatically, magnetically, by temperature changes, or by another type of a drive unit. An adjustment of the angle of the mirror element to the surface to be recorded of the object(s) and/or to the object(s) may thus be performed easily, under the influence of larger or smaller friction forces which brake the movement. Precisely in the event of the preferred use of a magnetic field for holding and adjusting and/or pivoting the mirror element, a movement is possible nearly without negative influence of friction forces, because the mirror element is more or less held floating in space.

The mirror element is advantageously implemented as a stable silvered plate, in particular a glass, metal, or plastic plate, in particular having a comparatively low weight, to allow a light, but simultaneously precise movement. The mirror element preferably has a very smooth recording surface having a particularly low roughness. In this way, a particularly exact reproduction of the objects to be recorded is possible for recording by the camera. To be able to compensate for distortions caused by irregularities on the mirror element, the analysis unit advantageously has a corresponding compensation unit, using which the distortions may be compensated for in the analysis.

The camera is preferably oriented essentially in a horizontal position approximately parallel to the surface of the object to be recorded. With such an orientation, the mirror element(s) may be situated in relation to one another in such a way that the movement of the mirror element may be recorded very well by the camera, without the mirror element obstructing the image recording by the camera during its movement.

The camera may be an analog or digital camera having imaging optics, the selection of the imaging optics being able to be tailored suitably to the particular application. Furthermore, a focusing and/or aperture adjustment unit which may be actuated manually or by a motor may be provided in the area of the imaging optics of the camera. In this way, adaptation to different distances to the object to be recorded is possible.

To obtain especially good lighting of the surface recorded by the at least one mirror element, an illumination unit is advantageously provided in the area of the camera. It has been proven to be especially advantageous to design the illumination unit as annular and enclosing the objective of the camera, because the objective of the camera is typically oriented optimally to the mirror element, to be able to record images recorded therein. The light is redirected to the object by its reflection in the mirror element and thus illuminates the areas to be recorded on the surface of the object.

The device according to the present invention and the method according to the present invention may be used in greatly varying fields of application. The use of the device for recording flaws on substrates, in particular flawed soldered points, missing or incorrectly positioned components, bridges, excess solder, solder beads, and/or codes has been proven to be especially advantageous. The device is especially also suitable for more difficult applications, in which errors are only recognizable or detectable with difficulty or codes are provided alternately at greatly varying points, particularly because of the high scanning speed and the high precision of the recorded data thus possible.

However, the use of the device according to the present invention is also suitable in buildings, rooms, or in public places for monitoring the buildings, rooms, or public places, in particular for monitoring a main hall of a bank, of department stores, filling stations, power plants, or other buildings or spaces to be monitored and/or for monitoring public places, in particular railway stations, airports, stadiums, etc.

Furthermore, the device according to the present invention and/or the method according to the present invention may advantageously also be used, for example, for quality control, in particular for printed image checking, completeness checking of constructed or produced products, connection point checking, in particular weld seam control, surface inspection, or for checking the correctness of other features of a product.

The use of the device according to the present invention and/or the method according to the present invention is also suitable for measuring objects, in particular components or parts thereof, in particular openings, holes, punches, or other object parts or objects to be measured, as well as buildings.

The object recording step for recording the object(s) to be recorded may be performed adjustably at regular or irregular time intervals. It is preferably adaptable or adapted to the frequency of a change of the object to be recorded. It is possible in this way to provide time-efficient recording of the objects, which provides an object recording step not continuously, but rather at time intervals tailored to the particular application. In particular, during the scanning and/or recording of objects on a transport belt, the frequency of the recording and thus of the movement of the mirror element are adapted to the speed of the transport belt, while in contrast if a room is monitored, for example, an adaptation to the expected changing frequency of the objects in this room is provided.

If objects which are alternately located at different positions are to be recorded by the device according to the present invention, it has been proven to be advantageous to provide a device, using which is possible to provide an object recognition step. This is performed before the actual scanning or object recording step in order, upon recognizing a positioning of the objects unknown in regard to objects to be read out or recorded, to store the new positioning and/or the new pattern of the surface of the object(s) in a databank for comparison to a scanned object surface. The position of the objects to be recorded is thus stored in a databank as a pattern and a comparison is performed in regard to the known pattern before or during, possibly also after each recording procedure (scanning procedure). If it proves that the pattern is not yet contained in the databank, a new pattern is stored. Particularly when recording codes on substrates, such as circuit boards, the codes may alternately be provided at different points, a recording procedure providing the recording of multiple codes on one or more substrates at once. To allow the most optimum possible recording and/or optimum readout of the codes, their position is optimally previously known, i.e., recorded by an object recognition step, so that they may be read out correctly, because the adjustment or pivoting unit for moving the mirror element moves it into the suitable position(s).

Precisely when monitoring very large rooms or rooms constructed with angles, multiple devices may also be provided, at least one of which is a device designed according to the present invention having a single camera and at least one mirror element assigned thereto. Because of the especially good adjustability of the mirror element, however, large rooms to be recorded may also be monitored using only one device according to the present invention.

In addition to the x axis adjustment or pivoting unit for adjusting and/or pivoting the mirror element around the x axis and the y axis adjustment or pivoting unit for adjusting or pivoting the mirror element around the y axis, a z axis adjustment unit may also be provided for adjusting the mirror element in the z direction, i.e., for moving the mirror element towards and away from the object to be recorded. If the device is situated too close to the object to be recorded, fuzziness may occur when recording some objects lying outside the set focus and thus corruption of the results or an impossible read out due to the different distances during the movement of the mirror element. This may be remedied by the selection of the largest possible distance to the overall area on which the objects to be recorded are situated. The differences of the distances to the objects to be recorded thus no longer differ in an amount which corrupts the measurement or makes readout of codes impossible, for example. Instead of selecting a suitably preset or pre-settable distance to the objects to be recorded, the distance may also be changed by the z axis adjustment unit even during the movement of the mirror element for recording and reading out the objects, so that focusing occurs. However, it is to be ensured for this purpose that it is still possible for the camera to record the image recorded in the mirror element and the movement of the mirror element occurs sufficiently calmly to avoid fuzziness during the imaging, which may otherwise result in readout errors and/or measurement irregularities. The analysis unit may also comprise at least one unit for compensating for perspective distortions, so that at least perspective distortions may be compensated for during the analysis of the recorded images in the analysis unit.

BRIEF DESCRIPTION OF THE DRAWINGS

In the following, exemplary embodiments of the present invention are described on the basis of the drawings to explain the present invention in greater detail.

DETAILED DESCRIPTION OF THE INVENTION

Figure 1:
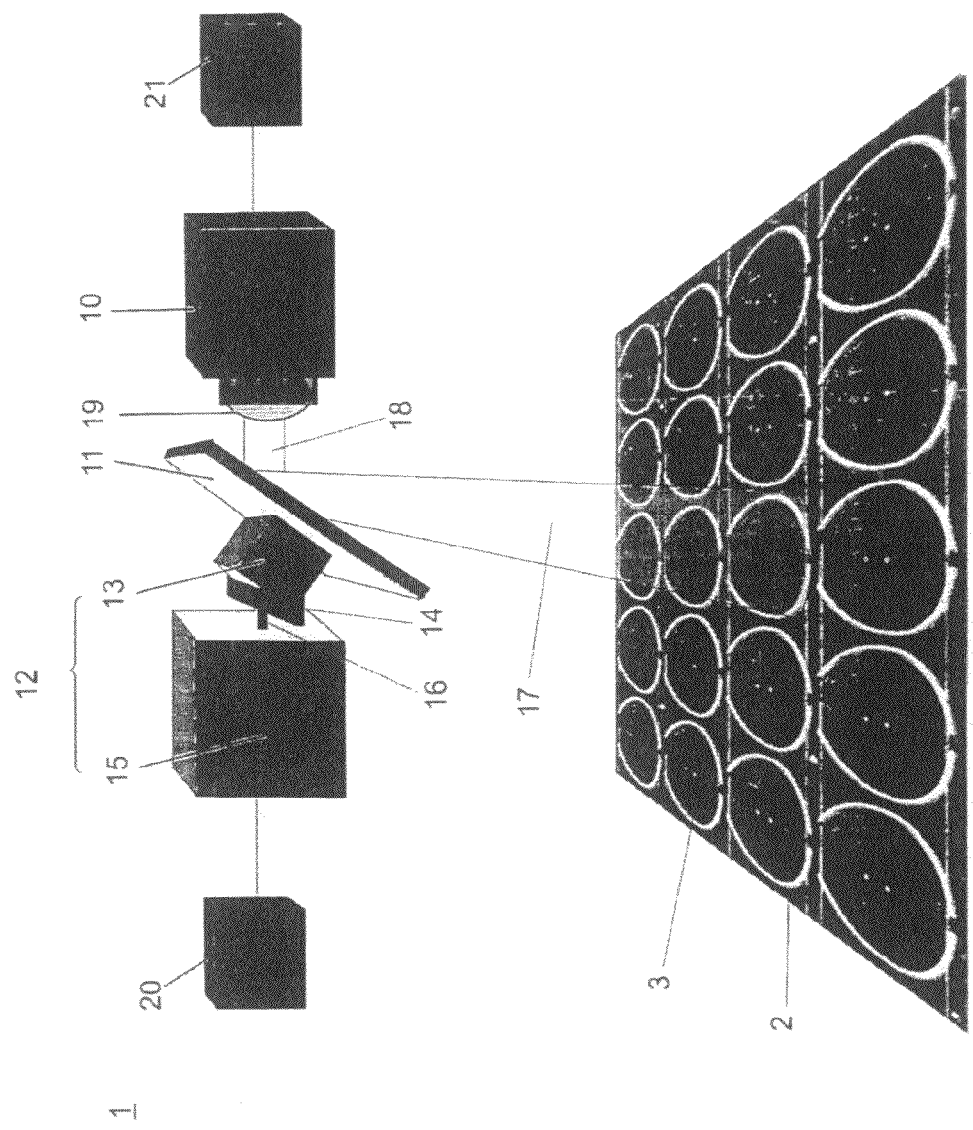
FIG. 1 shows a perspective schematic sketch of a first embodiment of a device according to the present invention for visually recording two-dimensional or three-dimensional objects, in the illustrated case soldered points on circuit boards.

FIG. 1 shows a perspective view of a first embodiment of a device 1 according to the present invention for visually recording objects, which are circuit boards 2 on the substrate 3 in the illustrated case. 20 such circuit boards 2 are situated on the substrate to be scanned, the soldered points on the circuit boards being checked.

The device 1 comprises a horizontally situated camera 10 and a mirror element 11. The latter is adjustable and/or pivotable in its position by an adjustment and/or pivoting unit 12, the angle to the plane of the substrate 3 and the objects to be recorded, the soldered points on the circuit boards 2, may thus be changed. The adjustment and/or pivoting unit 12 comprises a unit 13 for pivoting the mirror element 11 around the x axis 14 and a unit 15 for pivoting the mirror element 11 around the y axis 16. Sufficient mobility is provided by the pivoting of the mirror element around the x and the y axes to be able to scan and/or record all circuit boards on the substrate during one recording step. The units 13 and 15 may be, for example, motors, in particular stepping motors, pneumatic units, hydraulic units, units which generate a magnetic field, units based on an adjustment by temperature change, in particular using thermoelements, etc.

The camera is oriented to the mirror element in such a way that it may record the images recorded thereby directly itself, which is indicated by the beam bundles 17 and 18 in FIG. 1. In the basic position before the recording procedure, during which the mirror element is pivoted around the x and y axes, the camera having its objective 19 as the imaging optics may be oriented approximately on the center of the mirror element.

An activation unit 20 (only indicated in FIG. 1) is provided for activating the adjustment and/or pivoting unit 12. Not only is the movement of the units 13 and 15 caused thereby, but rather the speed of the movement of the mirror element and the dimension of its movement around the x and y axes may be adapted to the change of the objects to be recorded and/or scanned, in particular also by the frequency of scanning, i.e., the repetition rate of the object recording steps.

The recorded data is relayed from the camera to an analysis unit 21, which is also only indicated in FIG. 1. This unit is advantageously also connected to the activation unit 19, to be able to perform another recording step if faulty recording of the data is established, before the substrate having the circuit boards is replaced with another one. For this purpose, a transport unit for moving the substrate may also be coupled to the analysis unit and/or activation unit in regard to the speed of the further transport of the substrate, in order to also adapt the individual components to one another here and thus achieve optimal recording of the object to be recorded, e.g., flawed soldered points.

The pivoting of the mirror element according to the present invention proves to be advantageous precisely when recording flawed soldered points, because scanning occurs from different viewing angles and thus shadows around the soldered points may also be used for the analysis if illumination of the substrate and/or the circuit boards is provided.

Figure 2:
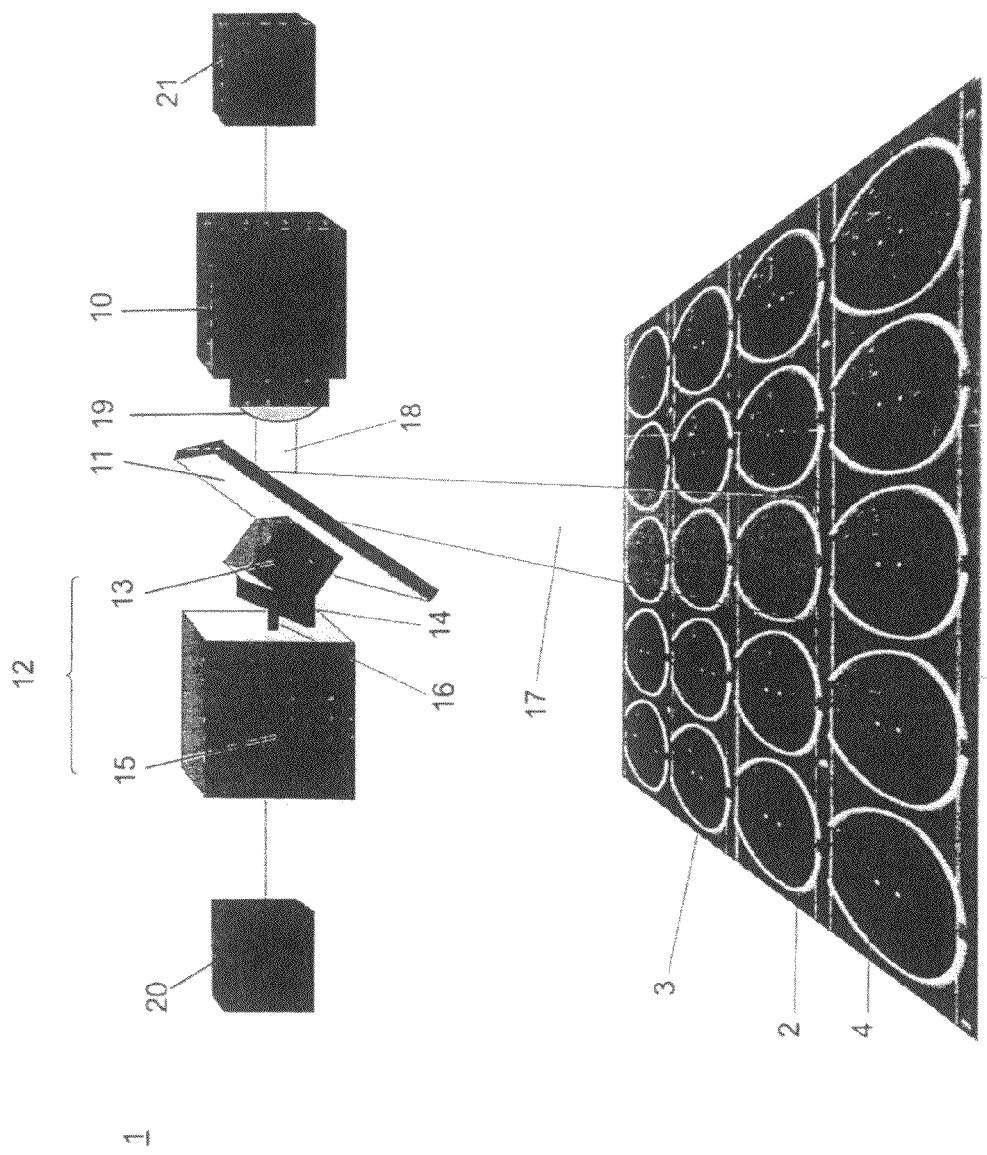
FIG. 2 shows a perspective schematic sketch of a second embodiment of a device according to the present invention for visually recording two-dimensional or three-dimensional objects, in the illustrated case for reading out codes on circuit boards.

Instead of checking the circuit boards for possible flawed soldered points, as shown in FIG. 1, readout of codes 4 on the circuit boards 2 by the device is provided in FIG. 2. Codes 4 of this type contain the production dates of products, for example. They may be positioned differently on the circuit boards and thus also on the substrate, as indicated in FIG. 2, so that readout using a measurement construction known in the prior art is hardly possible. Only by providing the combination according to the present invention of a stationary camera and a moved mirror element, however, is it possible to read out the very small codes without problems.

In addition to the embodiments of a device and a method for visually recording two-dimensional or three-dimensional objects described above and shown in the drawing, numerous further embodiments may be produced, in each of which only one single camera in connection with at least one mirror element is sufficient for rapidly recording a large area and/or a large space.

LIST OF REFERENCE NUMERALS

1 device
2 circuit board
3 substrate
4 code
10 camera
11 mirror element
12 adjustment and/or pivoting unit
13 unit for pivoting the mirror element around the x axis
14 x axis
15 unit for pivoting the mirror element around the y axes
16 y axis
17 beam bundle
18 beam bundle
19 objective
20 activation unit
21 analysis unit

The invention claimed is:

1. A device for visually recording two-dimensional or three-dimensional objects, which comprises: one single camera provided as positionally fixed for recording images of the two-dimensional or three-dimensional object and provided with or connectable or connected to at least one analysis unit for analyzing the recorded images, and only one mirror element is provided and is adjustable or pivotable around at least two axes by an adjustment or pivoting unit.

2. The device according to claim 1, wherein an activation unit is provided for the adjustment or pivoting unit for activating the adjustment or pivoting unit for the mirror element using a predefinable or predefined program.

3. The device according to claim 1, wherein the adjustment or pivoting unit comprises at least one unit for adjusting or pivoting the mirror element around a x axis and at least one unit for adjusting or pivoting the mirror element around a y axis, the units being provided separately from one another or in combination with one another.

4. The device according to claim 3, wherein the x axis adjustment or pivoting unit for adjusting or pivoting the mirror element around the x axis and/or the y axis adjustment or pivoting unit for adjusting the mirror element around the y axis is or are drivable or driven by motor, hydraulically, pneumatically, magnetically, by temperature changes, or by another type of a drive unit.

5. The device according to claim 1, wherein the camera is oriented essentially in a horizontal position approximately parallel to the surface of the object to be recorded.

6. The device according to claim 1, wherein the camera is an analog or digital camera having imaging optics.

7. The device according to claim 6, wherein a focusing or aperture adjustment unit or a combination thereof, which may be actuated manually or by a motor, is provided in the area of the imaging optics of the camera.

8. The device according to claim 1, wherein multiple devices are provided, at least one of which comprises one single camera and at least one mirror element assigned thereto.

9. The device according to one of the preceding claims claim 1, wherein an illumination unit is provided in an area of the camera.

10. The device according to claim 9, wherein the illumination unit is annular and encloses an objective of the camera.

11. The device according to claim 3, wherein a z axis adjustment unit is provided for adjusting the mirror element in the z direction to move the mirror element towards and away from the object to be recorded.

12. The device according to claim 1, wherein the analysis unit comprises at least one unit for compensating for perspective distortions.

13. A method for visually recording two-dimensional or three-dimensional objects using a device, comprising the steps of:
   situating a fixed position camera and only one mirror element of the device that is adjustable around at least two axes in relation to one another in such a way that the objects to be recorded are situated in a recording area of the one mirror element,
   adjusting or pivoting the adjustable mirror element around one or two axes at an adjustable speed to record the objects to be recorded, wherein the camera records the objects imaged in the one mirror element, and
   relaying the recorded objects from the camera to an analysis unit for analysis and processing the recorded objects.

14. The method according to claim 13, wherein the adjustment or pivoting of the at least one mirror element occurs at a high speed of at least 20 objects per second.

15. The method according to claim 14, wherein the adjustment or pivoting of the at least one mirror element occurs at a speed of 50 objects per second.

16. The method according to claim 1, wherein the precision of the recording is at least 1/100 mm, in particular 1/1000 mm.

17. The method according to claim 13, wherein the object recording step for recording the object(s) to be recorded occurs at regular or irregular time intervals, and in particular is adaptable or adapted to the frequency of a change of the objects to be recorded.

18. The method according to claim 13, wherein upon recognizing a positioning of the objects to be read out or recorded which is unknown, an object recognition step is performed before the object recording step.

19. The method according to claim 13, further comprising the step of recording flaws on substrates with the device.

20. The method according to claim 13, further comprising the step of monitoring buildings or rooms with the device.

21. The method according to claim 13, further comprising the step of checking a printed image, checking completeness of constructed or produced products, checking a connection point, checking a weld seam, inspecting a surface, or checking the correctness of other features of a product with the device.

22. The method according to claim 13, further comprising measuring objects, components or parts of objects, openings, holes, punches, or other object parts with the device.

* * * * *